US008921536B2

(12) United States Patent
Weiner et al.

(10) Patent No.: US 8,921,536 B2
(45) Date of Patent: Dec. 30, 2014

(54) HCV VACCINES AND METHODS FOR USING THE SAME

(75) Inventors: David B Weiner, Merion, PA (US); Krystle Lang, Philadelphia, PA (US); Jian Yan, Havertown, PA (US); Ruxandra Draghia-Akli, Brussels (BE); Amir S Khan, Narberth, PA (US)

(73) Assignees: The Trustees of the University of Pennsylvania, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 315 days.

(21) Appl. No.: 13/278,160

(22) Filed: Oct. 20, 2011

(65) Prior Publication Data

US 2012/0093863 A1    Apr. 19, 2012

Related U.S. Application Data

(63) Continuation-in-part of application No. 13/127,008, filed as application No. PCT/US2008/081627 on Oct. 29, 2008, now Pat. No. 8,829,174.

(51) Int. Cl.
| | |
|---|---|
| *C07H 21/04* | (2006.01) |
| *A61K 48/00* | (2006.01) |
| *A61K 31/711* | (2006.01) |
| *A61K 39/29* | (2006.01) |
| *A61K 38/00* | (2006.01) |
| *A61K 39/00* | (2006.01) |

(52) U.S. Cl.
CPC ............... *A61K 31/711* (2013.01); *A61K 39/29* (2013.01); *A61K 38/00* (2013.01); *C07K 2319/02* (2013.01); *C12N 2770/24234* (2013.01); *A61K 2039/53* (2013.01)
USPC .......................................... 536/23.1; 514/44

(58) Field of Classification Search
CPC A61K 39/29; A61K 2039/51; A61K 2039/53
See application file for complete search history.

(56) References Cited

U.S. PATENT DOCUMENTS

| | | | |
|---|---|---|---|
| 4,510,245 | A | 4/1985 | Cousens et al. |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | Davis et al. |
| 4,945,050 | A | 7/1990 | Sanford et al. |
| 5,017,487 | A | 5/1991 | Stunnenberg et al. |
| 5,036,006 | A | 7/1991 | Sanford et al. |
| 5,077,044 | A | 12/1991 | Stocker et al. |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali et al. |
| 5,294,441 | A | 3/1994 | Curtiss, III |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Gurtiss, III |
| 5,424,065 | A | 6/1995 | Curtiss, III et al. |
| 5,451,499 | A | 9/1995 | Cochran |
| 5,453,364 | A | 9/1995 | Paoletti |
| 5,462,734 | A | 10/1995 | Letchworth, III et al. |
| 5,470,734 | A | 11/1995 | Sondermeijer et al. |
| 5,474,935 | A | 12/1995 | Chatterjee et al. |
| 5,482,713 | A | 1/1996 | Paoletti |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,127,116 | A | 10/2000 | Rice et al. |
| 6,156,319 | A | 12/2000 | Cohen et al. |

(Continued)

FOREIGN PATENT DOCUMENTS

WO            94/16737        8/1994

OTHER PUBLICATIONS

Guruprasad et al. Correlation between stability of a protein and its dipeptide composition: a novel approach for predicting in vivo stability of a protein from its primary sequence. Protein Eng. Dec. 1990;4(2):155-61.*
Einav et al. A nucleotide binding motif in hepatitis C virus (HCV) NS4B mediates HCV RNA replication. J Virol. Oct. 2004;78(20):11288-95.*
Meyer-Olson et al. Limited T cell receptor diversity of HCV-specific T cell responses is associated with CTL escape. J Exp Med. Aug. 2, 2004;200(3):307-19.*
Weiner, A.J. et al., "Intrahepatic genetic inoculation of hepatitis C virus RNA confers cross-protective immunity", J Virol, 2001, 75:7142-5148.
Bassett, S.E. et al., "Protective immune response to hepatitis C virus in champanzees rechallenged following clearance of primary infection", Hepatology, 2001, 33:1479-1487.

(Continued)

Primary Examiner — Michelle S Horning
(74) Attorney, Agent, or Firm — Riverside Law LLP

(57) ABSTRACT

Improved anti-HCV immunogens and nucleic acid molecules that encode them are disclosed. Immunogens disclosed include those having consensus HCV genotype 1a, including for example, NS4B, NS5A and NS5B. Pharmaceutical composition, recombinant vaccines comprising and live attenuated vaccines are disclosed as well methods of inducing an immune response in an individual against HCV are disclosed.

10 Claims, 8 Drawing Sheets

(56) References Cited

U.S. PATENT DOCUMENTS

| | | | |
|---|---|---|---|
| 6,589,529 | B1 | 7/2003 | Choi et al. |
| 7,245,963 | B2 | 7/2007 | Draghia-Akli et al. |
| 2002/0004048 | A1* | 1/2002 | Ralston et al. ............. 424/189.1 |
| 2004/0247615 | A1 | 12/2004 | Emini et al. |
| 2005/0052630 | A1 | 3/2005 | Smith et al. |
| 2006/0093617 | A1 | 5/2006 | Buyse et al. |
| 2008/0091135 | A1 | 4/2008 | Draghia-Akli et al. |

OTHER PUBLICATIONS

Lanford, R.E. et al., "Cross-genotype immunity to hepatitis C virus", J. Virol, 2004, 78:1575-1581.

Houghton, M. et al., "Prospects for a vaccine against the hepatitus C virus", Nature, 2005, 436:961-966.

Frelin, L. et al., "Low dose and gene gun immunization with a hepatitis C virus nonstructural (NS) 3 DNA-based vaccine containing NS4A inhibit NS3/4A-expressing tumors in vivo", Gene Therapy, 2003, 10:686-699.

Wolk, B. et al. "Subcellular localization, stability, and trans-cleavage competence of the hepatitis C virus NS3-NS4A complex expressed in tetracycline-regulated cell lines", J. Virol., 2000, 74:2293-2304.

Tanji, Y et al., "Hepatitis C virus-encoded nonstructural protein NS4A has versatile functions in viral protein processing", J. Virol., 1995, 36:1575-1581.

Cooper, S. et al., "Analysis of a successful immune response against hepatitis C virus", Immunity, 1999, 10:439-449.

Post, J.J. et al., "Clearance of hepatitis C viremia associated with cellular immunity in the absence of seroconversion in the hepatitis C incidence and transmission in prisons study cohort", J. Infect Dis., 2004, 189:1846-1855.

Lechner, F. et al., "Analysis of successful immune responses in persons infected with hepatitis C virus", J Exp Med, 2000, 191:1499-1512.

Rehermann, B. et al., "Quantitative analysis of the peripheral blood cytotoxic T lymphocyte response in patients with chronic hepatitis C virus infection", J Clin Invest, 1996, 98:1432-1440.

Thimme, R. et al., "Determinants of viral clearance and persistence during acute hepatitis C virus infection", J Exp Med. 2001, 194:1395-1406.

Nelson, D.R. et al., "The role of hepatitis C virus-specific cytotoxic T lymphocytes in chronic hepatitis C", J Immunol, 1997, 158:1473-1481.

Missale, G. et al., "Differenct clinical behaviors of acute hepatitis C virus infection are associated with different vigor of the anti-viral cell-mediated immune response", J Clin Invest, 1996, 98:706-714.

Diepolder, H.M. et al., "Possible mechanism involving T-lymphocyte response to non-structural protein 3 in viral clearance in acute hepatitis C virus infection", Lancet, 1995, 346:1006-1007.

Chattergoon, M. et al., "Genetic immunization: a new era in vaccines and immune therapeutics", FASEB J, 1997, 11:753-763.

Liu, M.A. et al., "Human clinical trials of plasmid DNA vaccines", Adv Genet, 2005, 55:25-40.

Capone, S et al., "Modulation of the immune response induced by gene electrotransfer of a hepatitis C DNA vaccine in nonhuman primates", J Immunol, 2006, 177:7462-7471.

Yan, J. et al., "Enhanced cellular immune responses elicited by an engineered HIV-1 subtype B consensus-based envelope DNA vaccine", Mol Ther, 2007, 15:411-421.

Ahlen, G. et al., "In vivo electroporation enhances the immunogenicity of hepatitis C virus nonstructural 3/4A DNA by increased local DNA uptake, protein expression, inflammation, and infiltration of CD3+ T cells", J Immunol, 2007, 179:4741-4753.

Frelin, L. et al., "Codon optimization and mRNA amplification effectively enhances the immunogenicity of the hepatitis C virus nonstructural 3/4A gene", Gene Therapy, 2004, 11:522-533.

Lang, K.A. et al., "Strong HCV NS3- and NS4A-specific cellular immune responses induced in mice and Rhesus macaques by a novel HCV genotype 1a/1b consensus DNA vaccine", Vaccine 2008, 26:6225-6231.

\* cited by examiner

HCV VACCINES AND METHODS FOR USING THE SAME

This application is a Continuation-In-Part of U.S. patent application Ser. No. 13/127,008, filed Apr. 29, 2011, of which U.S. patent application Ser. No. 13/127,008 is a National Stage filing of PCT Application No. PCT/US08/81627, the disclosures of which are each incorporated herein by reference.

FIELD OF THE INVENTION

The present invention relates to improved HCV antigens and vaccines made therefrom, and improved methods for inducing immune responses, and prophylactically and/or therapeutically immunizing individuals against HCV.

BACKGROUND OF THE INVENTION

Hepatitis C(HCV) is a small enveloped, positive stranded RNA virus that represents a major health burden worldwide with more than 170 million individuals currently infected [Thomson, B. J. and R. G. Finch, Hepatitis C virus infection. Clin Microbiol Infect, 2005. 11(2): p. 86-94]. One of the most successful of all human viruses, HCV preferentially infects heptocytes and is able to persist in the livers of up to 70% of all infected individuals [Bowen, D. G. and C. M. Walker, Adaptive immune responses in acute and chronic hepatitis C virus infection. Nature, 2005. 436(7053): p. 946-52]. It is estimated that up to 30% of chronically infected individuals will develop progressive liver disease, including cirrhosis and heptocellular carcinoma (HCC) during their lifetime making HCV infection the leading causes of liver transplantation in the world. In addition, HCV and HBV infections are implicated in 70% of all cases of HCC, which is the third leading cause of cancer deaths worldwide [Levrero, M., Viral hepatitis and liver cancer: the case of hepatitis C. Oncogene, 2006. 25(27): p. 3834-47].

Due to the persistent nature of the virus, HCV infection can be extremely difficult and expensive to treat. Most infected individuals do not receive treatment. However, those that do, pay on average $17,700 to 22,000 US for standard treatment protocols [Salomon, J. A., et al., Cost-effectiveness of treatment for chronic hepatitis C infection in an evolving patient population. Jama, 2003. 290(2): p. 228-37]. Genotype 1 infection, the most prevalent in Europe and North America, has the poorest prognosis with as little as 42% of individuals responding to standard treatments [Manns, M. P., et al., Peginterferon alfa-2b plus ribavirin compared with interferon alfa-2b plus ribavirin for initial treatment of chronic hepatitis C: a randomised trial. Lancet, 2001. 358(9286): p. 958-65].

Therefore, the high prevalence of infection, lack of effective treatments and economic burden of chronic HCV, illustrates the urgent need for the development of novel immune therapy strategies to combat this disease. Currently there is no prophylactic or therapeutic vaccine for HCV.

Understanding the adaptive immunity to this virus is critical for designing strategies, such as DNA vaccines, to combat viral infection. Although virus-specific antibodies are detected within 7-8 weeks post HCV infection [Pawlotsky, J. M., Diagnostic tests for hepatitis C. J Hepatol, 1999. 31 Suppl 1: p. 71-9] they do not protect against reinfection [Farci, P., et al., Lack of protective immunity against reinfection with hepatitis C virus. Science, 1992. 258(5079): p. 135-40; Lai, M. E., et al., Hepatitis C virus in multiple episodes of acute hepatitis in polytransfused thalassaemic children. Lancet, 1994. 343(8894): p. 388-90] and can be completely absent following the resolution of infection [Cooper, S., et al., Analysis of a successful immune response against hepatitis C virus. Immunity, 1999. 10(4): p. 439-49; Post, J. J., et al., Clearance of hepatitis C viremia associated with cellular immunity in the absence of seroconversion in the hepatitis C incidence and transmission in prisons study cohort. J Infect Dis, 2004. 189(10): p. 1846-55].

Thus, one of the major challenges in vaccine development for HCV is that unlike other hepatitis viruses, such as Hepatitis A and Hepatitis B, where successful antibody-based vaccines have been created, protection against HCV infection does not appear to be antibody mediated. Although the exact correlates of immune protection remain to be elucidated, numerous studies of both acutely infected patients and chimpanzees, have provided compelling evidence that strong T helper 1 (Th1) responses directed against the more genetically conserved non-structural regions of the virus are associated with clearance of HCV infection. See Missale, G., et al., *Different clinical behaviors of acute hepatitis C virus infection are associated with different vigor of the anti-viral cell-mediated immune response*. J Clin Invest, 1996. 98(3): p. 706-14; and Diepolder, H. M., et al., *Possible mechanism involving T-lymphocyte response to non-structural protein 3 in viral clearance in acute hepatitis C virus infection*. Lancet, 1995. 346(8981): p. 1006-7. Also, importantly, it has been shown that localization of HCV-specific T cells to the liver rather than peripheral blood is critical for both reduction in viral load and clearance of acute infection. See Thimme, R., et al., *Determinants of viral clearance and persistence during acute hepatitis C virus infection*. J Exp Med, 2001. 194(10): p. 1395-406; and Shoukry, N. H., et al., *Memory CD8+ T cells are required for protection from persistent hepatitis C virus infection*. J Exp Med, 2003. 197(12): p. 1645-55

Furthermore, it appears that infected individuals that mount an early, multi-specific, intrahepatic CD4+ helper and CD8+ cytotoxic T-cell response tend to show elimination of HCV infection [Lechner, F., et al., Analysis of successful immune responses in persons infected with hepatitis C virus. J Exp Med, 2000. 191(9): p. 1499-512; Gerlach, J. T., et al., Recurrence of hepatitis C virus after loss of virus-specific CD4(+) T-cell response in acute hepatitis C. Gastroenterology, 1999. 117(4): p. 933-41; Thimme, R., et al., Determinants of viral clearance and persistence during acute hepatitis C virus infection. J Exp Med, 2001. 194(10): p. 1395-406; Grakoui, A., et al., HCV persistence and immune evasion in the absence of memory T cell help. Science, 2003. 302(5645): p. 659-62].

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platforms immunogenicity when moving to larger animals [Liu, M. A. and J. B. Ulmer, Human clinical trials of plasmid DNA vaccines. Adv Genet, 2005. 55: p. 25-40].

Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al, Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens may be able to increase the breadth of the cellular immune response as compared to native antigens alone [Yan., J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

DNA vaccines encoding HCV NS3 and NS4 are disclosed in Lang, K. A. et al. Vaccine vol 26, issue 49, pp 6225-6231 (November 2008).

Therefore, there still remains a need for an effective vaccine against HCV. Also, there still remains a need for effective methods of treating individuals infected with HCV.

SUMMARY OF THE INVENTION

Aspects of the present invention include nucleic acid molecules comprising a coding sequence encoding one or more proteins selected from the group comprising: a) SEQ ID NO:2; a protein that is 98% homologous to SEQ ID NO:2; or an immunogenic fragment of SEQ ID NO:2; b) SEQ ID NO:4; or a protein that is 98% homologous to SEQ ID NO:4; or an immunogenic fragment of SEQ ID NO:4; c) SEQ ID NO:6; a protein that is 98% homologous to SEQ ID NO:6; or an immunogenic fragment of SEQ ID NO:6. In some embodiments, the nucleic acid molecules can be absent of an encoding sequence of an IgE leader encoding SEQ ID NO:9. Preferably, the nucleic acid molecules can be one or more sequences selected from the group comprising: a) SEQ ID NO:1; or a coding sequence that is 98% homologous to SEQ ID NO:1; b) SEQ ID NO:3; or a coding sequence that is 98% homologous to SEQ ID NO:3; or c) SEQ ID NO:5; or a coding sequence that is 98% homologous to SEQ ID NO:5. In some embodiments, these nucleic acid molecules are absent of an encoding sequence of an IgE leader having sequence of SEQ ID NO:7 or SEQ ID NO:8.

Further, there are disclosed aspects that include methods of treating a subject diagnosed with HCV, comprising administering the nucleic acid molecules described herein to the subject.

In another aspect, there are proteins selected from the group consisting of: a) SEQ ID NO:2; a protein that is 98% homologous to SEQ ID NO:2; or an immunogenic fragment of SEQ ID NO:2; b) SEQ ID NO:4; a protein that is 98% homologous to SEQ ID NO:4; or an immunogenic fragment of SEQ ID NO:4; or c) SEQ ID NO:6; a protein that is 98% homologous to SEQ ID NO:6; or an immunogenic fragment of SEQ ID NO:6. In some embodiments, the proteins described herein can be absent of an IgE leader having sequence SEQ ID NO:9.

There are further described herein methods of treating a subject diagnosed with HCV, comprising administering the proteins herein.

Additional, there are pharmaceutical compositions described herein that comprise the nucleic acid molecules provided herein and a pharmaceutically acceptable excipient. Furthermore, there are pharmaceutical compositions that comprise the proteins provided herein and a pharmaceutically acceptable excipient.

BRIEF DESCRIPTION OF THE FIGURES

FIG. 8 shows plasmid maps of.

DETAILED DESCRIPTION OF PREFERRED EMBODIMENTS

Figure 1:
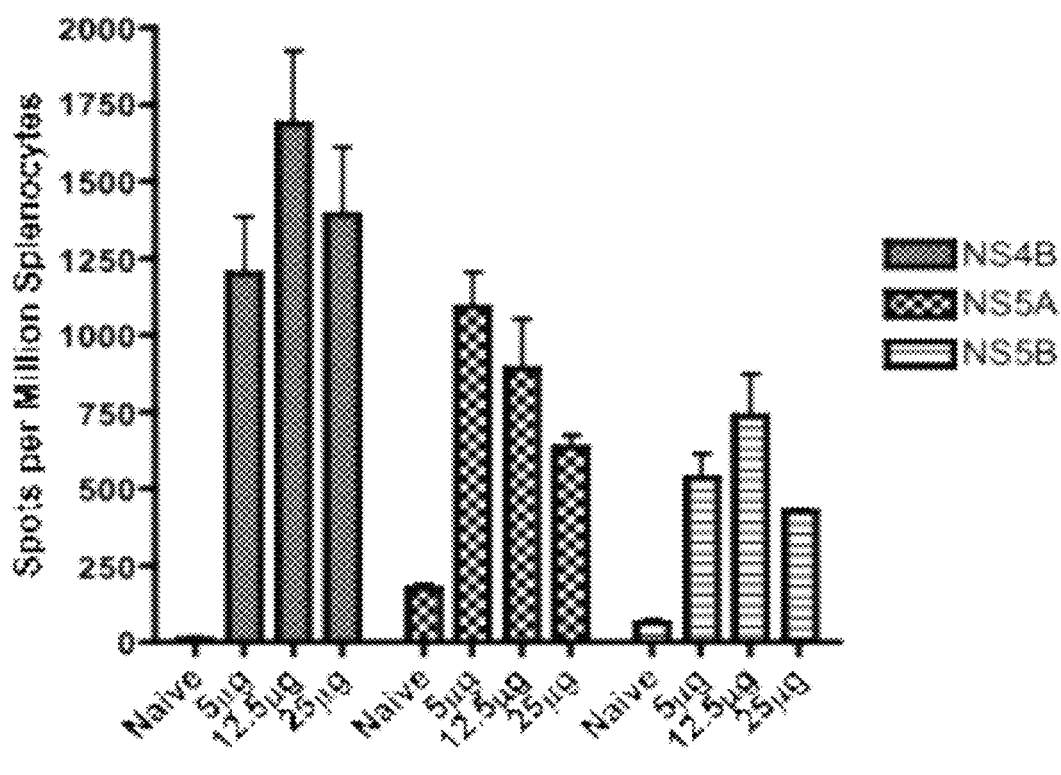
FIG. 1: Dose response for pConNS4B, pConNS5A and pConNS5B Animals (n=5) were immunized with either, 5 μg, 12.5 μg or 25 μg of either pConNS4B, pConNS5A and pConNS5B. Animals received a total of two intramuscular immunizations followed by electroporation with each immunization given two weeks apart. Animals were sacrificed one week following the last immunization after which the splenocytes were individually isolated and analyzed. The response of each individual animal was determined through the use of an IFN-γ ELISpot assay from which the optimum dose of each construct was determined.

As used herein, the phrase "stringent hybridization conditions" or "stringent conditions" refers to conditions under which a nucleic acid molecule will hybridize another a nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

Improved vaccine are disclosed which arise from a multi-step approach to design different DNA vaccines that can induce enhanced cellular immune responses, including, in particular, cytotoxic and IFN-γ and HCV-specific T cell responses directed against multiple conserved regions within the virus. Modified consensus sequences were generated, including for example, DNA vaccines that include consensus antigens NS4B, NS5A and NS5B. Genetic modifications including codon optimization, RNA optimization, and the addition of a high efficient immunoglobin leader sequence are also disclosed.

The improved HCV vaccines are based upon proteins and genetic constructs that encode proteins with epitopes that make them particularly effective as immunogens against which anti-HCV can be induced.

In some embodiments there are nucleic acid molecules comprising a coding sequence encoding one or more proteins selected from the group comprising: a) SEQ ID NO:2; a protein that is 98% homologous to SEQ ID NO:2; or an immunogenic fragment of SEQ ID NO:2; b) SEQ ID NO:4; or a protein that is 98% homologous to SEQ ID NO:4; or an immunogenic fragment of SEQ ID NO:4; c) SEQ ID NO:6; a protein that is 98% homologous to SEQ ID NO:6; or an immunogenic fragment of SEQ ID NO:6. In some embodiments, the nucleic acid molecules can be absent of an encoding sequence of an IgE leader encoding SEQ ID NO:9. Preferably, the nucleic acid molecules can be one or more sequences selected from the group comprising: a) SEQ ID NO:1; or a coding sequence that is 98% homologous to SEQ ID NO:1; b) SEQ ID NO:3; or a coding sequence that is 98% homologous to SEQ ID NO:3; or c) SEQ ID NO:5; or a coding sequence that is 98% homologous to SEQ ID NO:5. In some embodiments, these nucleic acid molecules are absent of an encoding sequence of an IgE leader having sequence of SEQ ID NO:7 or SEQ ID NO:8.

Accordingly, vaccines may induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination elected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against HCV. When a nucleic acid molecule that encodes the protein is taken up by cells of the individual the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

In another aspect, there are proteins selected from the group consisting of: a) SEQ ID NO:2; a protein that is 98% homologous to SEQ ID NO:2; or an immunogenic fragment of SEQ ID NO:2; b) SEQ ID NO:4; a protein that is 98% homologous to SEQ ID NO:4; or an immunogenic fragment of SEQ ID NO:4; or c) SEQ ID NO:6; a protein that is 98% homologous to SEQ ID NO:6; or an immunogenic fragment of SEQ ID NO:6. In some embodiments, the proteins described herein can be absent of an IgE leader having sequence SEQ ID NO:9.

Further, there are disclosed aspects that include methods of treating a subject diagnosed with HCV, comprising administering the nucleic acid molecules described herein to the subject.

There are further described herein methods of treating a subject diagnosed with HCV, comprising administering the proteins herein.

Additional, there are pharmaceutical compositions described herein that comprise the nucleic acid molecules provided herein and a pharmaceutically acceptable excipient. Furthermore, there are pharmaceutical compositions that comprise the proteins provided herein and a pharmaceutically acceptable excipient.

Compositions and methods are provided which prophylactically and/or therapeutically immunize an individual against HCV. Compositions for delivering nucleic acid molecules that comprise a nucleotide sequence that encodes the immunogen are operably linked to regulatory elements. Compositions may include a plasmid that encodes the immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

SEQ ID NO:1 comprises a nucleotide sequence that encodes an HCV genotype 1a consensus immunogen of HCV proteins NS4B. SEQ ID NO:1 further comprises an IgE leader sequence linked to the nucleotide sequence that encodes an HCV genotype 1a consensus immunogen of HCV proteins NS4B, along with additional 5' upstream sequences from the IgE leader. SEQ ID NO:2 comprises the amino acid sequence for the HCV genotype 1a consensus immunogen of HCV protein NS4B. SEQ ID NO:2 further comprises an IgE leader sequence linked to a consensus immunogen sequence. The IgE leader sequence is N-terminal to the consensus NS4B and is SEQ ID NO:9 and can be encoded by SEQ ID NO:8.

The consensus antigens described herein and the vaccines made therefrom can include, or have removed, the IgE leader sequences.

In some embodiments, vaccines preferably comprise SEQ ID NO:2 or a nucleic acid molecule that encodes it. In some embodiments, vaccines preferably comprise SEQ ID NO:1. Vaccines preferably include the IgE leader sequence SEQ ID NO:9 or nucleic acid sequence which encodes the same.

Homologous sequences of SEQ ID NO:1 may comprise 90 or more nucleotides. In some embodiments, fragments of SEQ ID NO:1 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, and in some embodiments, 870 or more nucleotides. In some embodiments, fragments of SEQ ID NO:1 may comprise coding sequences for the IgE leader sequences. In some embodiments, homologous sequences of SEQ ID NO:1 do not comprise coding sequences for the IgE leader sequences. Preferably, the homologous sequences have 90%, 91%, 92%, 93%, 94%, 95%, 96%, 97%, 98%, or 99% homology to SEQ ID NO:1, and more preferably 98%, or 99%. In some embodiments, there are immunogenic fragments of SEQ ID NO:1, and preferably fragments that have 90%, 91%, 92%, 93%, 94%, 95%, 96%, 97%, 98%, or 99% homology to SEQ ID NO:1, and more preferably, 98% or 99%.

Homologous sequences of SEQ ID NO:2 may comprise 30 or more amino acids. In some embodiments, fragments of SEQ ID NO:2 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; and in some embodiments, 270 or more amino acids. Preferably, the homologous sequences have 90%, 91%, 92%, 93%, 94%, 95%, 96%, 97%, 98%, or 99% homology to SEQ ID NO:2, and more preferably 98%, or 99%. In some embodiments, there are immunogenic fragments of SEQ ID NO:2, and preferably fragments that have 90%, 91%, 92%, 93%, 94%, 95%, 96%, 97%, 98%, or 99% homology to SEQ ID NO:2, and more preferably, 98% or 99%.

SEQ ID NO:3 comprises a nucleotide sequence that encodes an HCV genotype 1a consensus immunogen of HCV proteins NS5A. SEQ ID NO:4 comprises the amino acid sequence for the HCV genotype 1a consensus immunogen of HCV proteins NS5A. SEQ ID NO:3 further comprises an IgE leader sequence linked to the nucleotide sequence that encodes an HCV genotype 1a consensus immunogen of HCV proteins NS5A, along with additional 5' upstream sequences from the IgE leader. SEQ ID NO:4 comprises the amino acid sequence for the HCV genotype 1a consensus immunogen of HCV protein NS5A. SEQ ID NO:4 further comprises an IgE leader sequence linked to the consensus immunogen sequence NS5A. The IgE leader sequence is N-terminal to the consensus NS5A and is SEQ ID NO:9 and can be encoded by SEQ ID NO:7.

Homologous sequences of SEQ ID NO:3 may comprise 90 or more nucleotides. In some embodiments, fragments of SEQ ID NO:3 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides; and in some embodiments, 1430 or more nucleotides. Preferably, the homologous sequences have 90%, 91%, 92%, 93%, 94%, 95%, 96%, 97%, 98%, or 99% homology to SEQ ID NO:3, and more preferably 98%, or 99%. In some embodiments, there are immunogenic fragments of SEQ ID NO:3, and preferably fragments that have 90%, 91%, 92%, 93%, 94%, 95%, 96%, 97%, 98%, or 99% homology to SEQ ID NO:3, and more preferably, 98% or 99%.

Homologous sequences of SEQ ID NO:4 may comprise 30 or more amino acids. In some embodiments, fragments of SEQ ID NO:4 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; and, in some embodiments, 470 or more amino acids. Preferably, the homologous sequences have 90%, 91%, 92%, 93%, 94%, 95%, 96%, 97%, 98%, or 99% homology to SEQ ID NO:4, and more preferably 98%, or 99%. In some embodiments, there are immunogenic fragments of SEQ ID NO:4, and preferably fragments that have 90%, 91%, 92%, 93%, 94%, 95%, 96%, 97%, 98%, or 99% homology to SEQ ID NO:4, and more preferably, 98% or 99%.

SEQ ID NO:5 comprises a nucleotide sequence that encodes an HCV genotype 1a consensus immunogen of HCV proteins NS5B. SEQ ID NO:6 comprises the amino acid sequence for the HCV genotype 1a consensus immunogen of HCV proteins NS5B. SEQ ID NO:5 further comprises an IgE leader sequence linked to the nucleotide sequence that encodes an HCV genotype 1a consensus immunogen of HCV proteins NS5B, along with additional 5' upstream sequences from the IgE leader. SEQ ID NO:6 comprises the amino acid sequence for the HCV genotype 1a consensus immunogen of HCV protein NS5B. SEQ ID NO:6 further comprises an IgE leader sequence linked to the consensus immunogen sequence NS5B. The IgE leader sequence is N-terminal to the consensus NS5B and is SEQ ID NO:9 and can be encoded by SEQ ID NO:8.

Homologous sequences of SEQ ID NO:5 may comprise 90 or more nucleotides. In some embodiments, fragments of SEQ ID NO:5 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides; in some embodiments, 1440 or more nucleotides; in some embodiments, 1530 or more nucleotides; in some embodiments, 1620 or more nucleotides; in some embodiments, 1710 or more nucleotides; and in some embodiments, 1800 or more nucleotides. Preferably, the homologous sequences have 90%, 91%, 92%, 93%, 94%, 95%, 96%, 97%, 98%, or 99% homology to SEQ ID NO:5, and more preferably 98%, or 99%. In some embodiments, there are immunogenic fragments of SEQ ID NO:5, and preferably fragments that have 90%, 91%, 92%, 93%, 94%, 95%, 96%, 97%, 98%, or 99% homology to SEQ ID NO:5, and more preferably, 98% or 99%.

Homologous sequences of SEQ ID NO:6 may comprise 30 or more amino acids. In some embodiments, fragments of SEQ ID NO:6 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; and, in some embodiments, 600 or more amino acids. Preferably, the homologous sequences have 90%, 91%, 92%, 93%, 94%, 95%, 96%, 97%, 98%, or 99% homology to SEQ ID NO:6, and more preferably 98%, or 99%. In some embodiments, there are immunogenic fragments of SEQ ID NO:6, and preferably fragments that have 90%, 91%, 92%, 93%, 94%, 95%, 96%, 97%, 98%, or 99% homology to SEQ ID NO:6, and more preferably, 98% or 99%.

According to some embodiments, methods of inducing an immune response in individuals against an immunogen comprise administering to the individual the amino acid sequence for the HCV genotype 1a consensus immunogen of HCV proteins NS4B, NS5A, or NS5B, functional fragments thereof, or expressible coding sequences thereof, or combinations of the aforementioned. Some embodiments comprise an isolated nucleic acid molecule that encodes the amino acid sequence for the HCV genotype 1a consensus immunogen of HCV proteins NS4B, NS5A, or NS5B, or fragments thereof. Some embodiments comprise a recombinant vaccine that encodes the amino acid sequence for the HCV genotype 1a consensus immunogen of HCV proteins NS4B, NS5A, or NS5B or fragments thereof. Some embodiments comprise a subunit vaccine that comprises the amino acid sequence for the HCV genotype 1a consensus immunogen of HCV proteins NS4B, NS5A, or NS5B or fragments thereof. Some embodiments comprise a live attenuated vaccine and/or a killed vaccine that comprise the amino acid sequence for the HCV genotype 1a consensus immunogen of HCV proteins NS4B, NS5A, or NS5B.

Improved vaccines comprise proteins and genetic constructs that encode proteins with epitopes that make them particularly effective as immunogens against which anti-HCV immune responses can be induced, particularly induce intrahepatic HCV-specific T cell immunity. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments of the invention, a vaccine is delivered to an individual to modulate the activity of the individual's immune system and thereby enhance the immune response. When nucleic acid molecules that encodes the protein is taken up by cells of the individual the nucleotide sequence is expressed in the cells and the protein are thereby delivered to the individual. Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a. functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, K1LLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HCV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021, 579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct. In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of: CTACK, TECK, MEC and functional fragments thereof is administered to the individual.

The present invention is further illustrated in the following Example. It should be understood that this Example, while indicating embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. patents, U.S. applications, and references cited throughout this disclosure are hereby incorporated in their entirety by reference.

EXAMPLE

Example 1

Design and Expression of pConNS4B, pConNS5A and pConNS5B

Figure 8A:
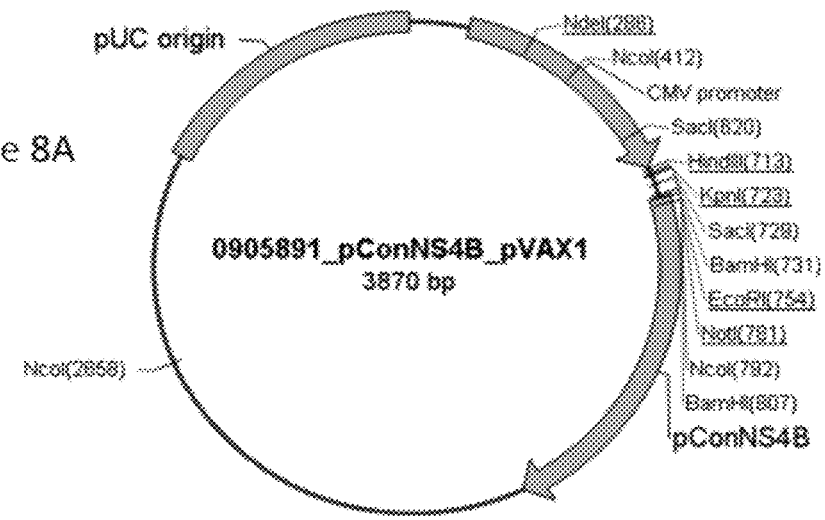
FIG. 8A expression construct pConNS4B_pVAX1, including consensus antigen NS4B.
Figure 8B:
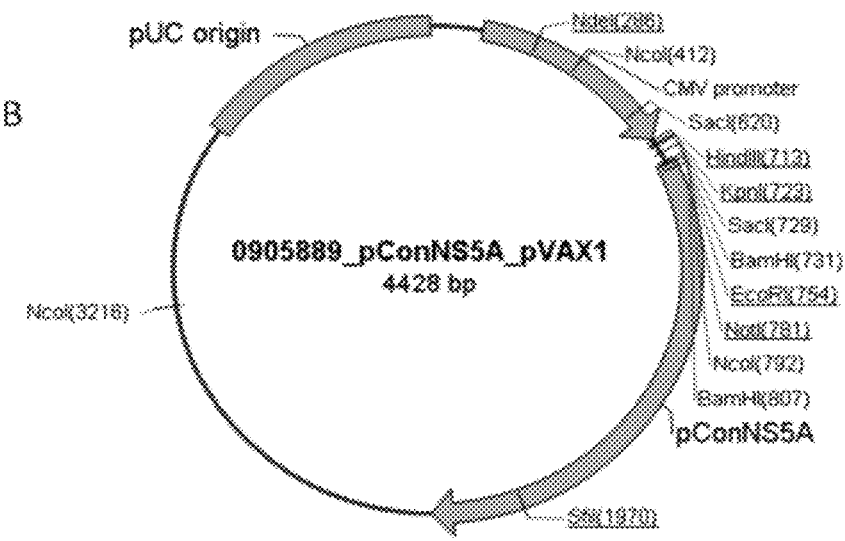
FIG. 8B expression construct pConNS5A_pVAX1, including consensus antigen NS5A.
Figure 8C:
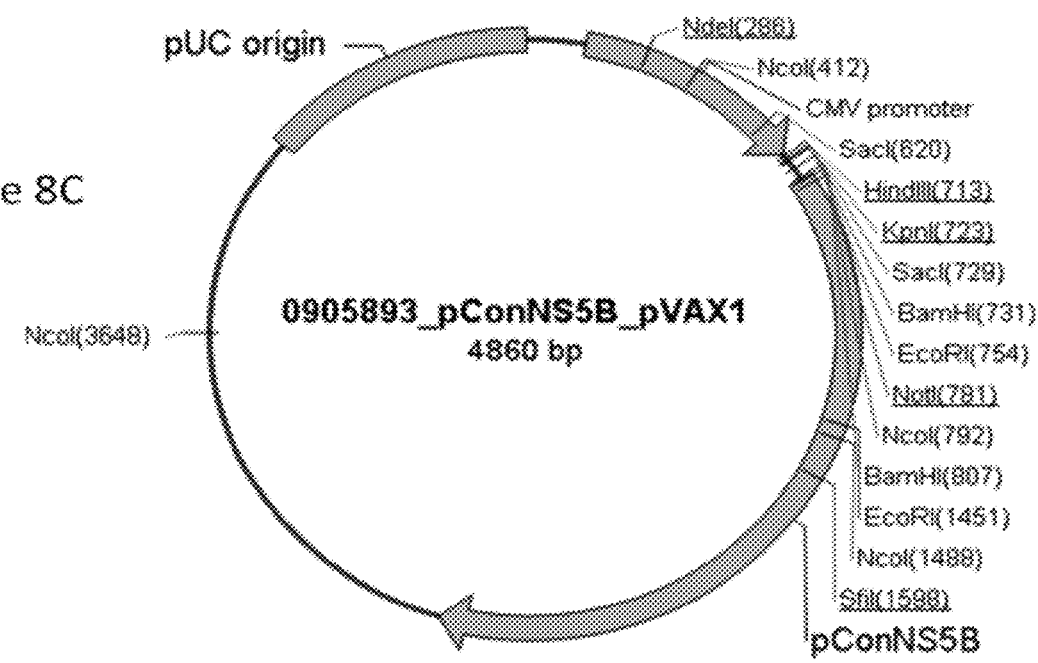
FIG. 8C expression construct pConNS5B_pVAX1, including consensus antigen NS5B.

The HCV genotype 1a consensus sequences for HCV proteins NS4B, NS5A and NS5B were generated from 170 different sequences obtained from the Los Alamos National Laboratory HCV Sequence Database. Several modification were then made to the consensus constructs in order to enhance their expression and detection, including the addition of IgE leader sequence at the C-term and an HA-tag at the N-term of each construct. Additionally, each construct was further modified through codon and RNA optimization using GeneOptimizer™ (GENEART, Germany) and subcloned in to the clinical expression vector pVAX under the control a CMV promoter. The final constructs were named pConNS4B, pConNS5A and pConNS5B (plasmid maps shown in FIGS. 8A-8C).

Protein expression of each construct was confirmed through transient transfection of human RD muscle cells with each individual construct. RD muscles cells were transiently transfected with pConNS4B, pConNS5A and pConNS5B using Lipofectamine™ (Invitrogen) according to the manufacturer's guidelines. Forty-eight hours following transfection, the cells were fixed and permeabilized. Expression of each protein was detected with an anti-HA polyclonal rabbit antibody (Invitrogen) followed by a Cy3 conjugated goat anti-rabbit secondary antibody (Invitrogen).

The cells were visualized using confocal microscopy and at 250× magnification (images not shown). All three constructs were shown to express, pConNS4B showed the highest number of transfected cells while pConNS5B showed the least. Transfection with the empty vector pVax was used as a control.

Example 2

Immunization of C57BL/6 Mice with pConNS4B, pConNS5A and pConNS5B Induces Strong Cellular Immune Responses Once expression of the constructs was confirmed, C57BL/6 mice were immunized in order to determine immunogenicity of the constructs. Six to eight week old female C57BL/6 mice were purchased from Jackson Laboratories and were maintained in accordance with the National Institutes of Health and the University of Pennsylvania Institutional Care and Use Committee (IACUC) guidelines. Animals were separated into three different dosing groups for each individual construct with five animals per group. The animals were immunized intramuscularly with either 5 µg, 12.5 µg or 25 µg of pConNS4B, pConNS5A or pConNS5B, followed by electroporation.

Electroporation was performed using the CELLECTRA™ adaptive constant current electroporation device and electrode arrays (Inovio Pharmaceuticals, Inc., Blue Bell, Pa.).

The animals received a total of two immunizations, two weeks apart and were sacrificed one week following the second immunization. The immunogenicity of the constructs was determine with the use of IFN-γ ELISpot assays.

The mouse IFN-γ ELISpot assays were conducted as previously described in Yan, J., et al., *Enhanced cellular immune responses elicited by an engineered HIV-1 subtype B consensus-based envelope DNA vaccine*. Mol Ther, 2007. 15(2): p. 411-21. The splenocytes were stimulated with pools of 15mer peptides over lapping by 8 amino acids and spanning the length of each construct. Peptides were synthesized by Genscript (Piscataway, N.J.), resuspended in DMSO and pooled at a concentration of 2 µg/ml/peptide. The splenocytes were plated at a concentration of 200,000 cells per well. Results were adjusted and graphed as the average number of spot forming units (SFU) per $1 \times 10^6$ splenocytes. The results of can be seen in FIG. 1.

The immunogenicity of the constructs correlated well with the constructs' expression levels as determined by immunoflorescence. While all constructs were strongly immunogenic, responses for pConNS4B were the largest while responses for pConNS5B were the least. The optimum dose; for pConNS4B was 12.5 μg (1687±237 SFU/10^6 splenocytes), for pConNS5A was 5 μg (1091±111 SFU/10^6 splenocytes) and for pConNS5B was 12.5 μg (736±136 SFU/10^6 splenocytes).

Once the dosing for each construct was determined, a more detailed analysis of the cellular immune responses induced by each construct was performed. The animals were immunized and grouped as previously described. Following sacrifice, the spleens were isolated and individually crushed with the use of a Stomacher device. The splenocytes were strained with a 40 μM cell strainer and treated 5 min with ACK lysis buffer (Biosource) to clear the RBCs. The splenocytes were resuspended in complete media (RPMI 1640 with 2 mM/L L-glutamine supplemented with 10% heat inactivated FBS, 1× anti-biotic/anti-mycotic, and 55 μM/L β-mercaptoethanol). Cell number was determined with a hemocytometer.

Figure 2:
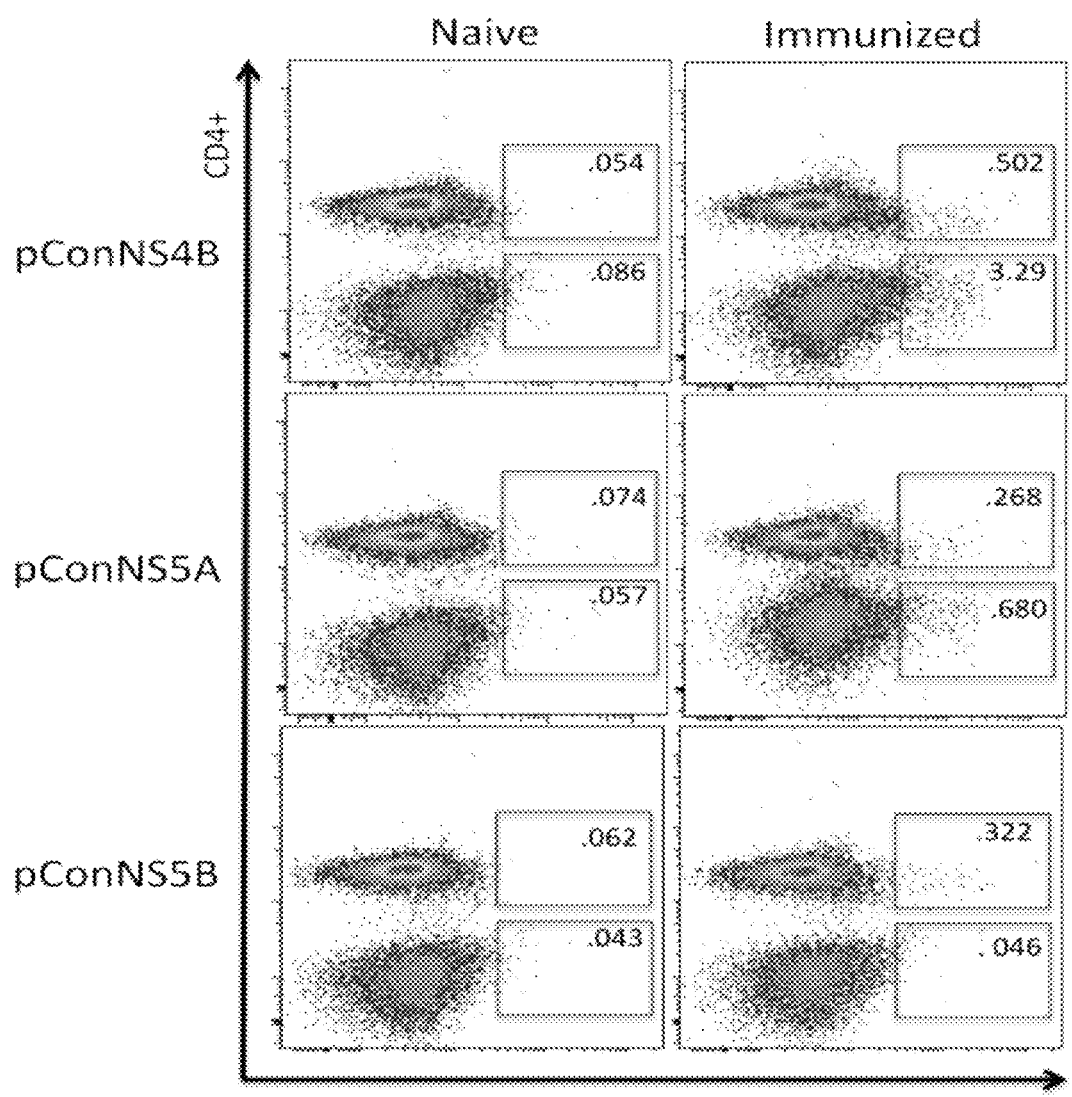
FIG. 2: Flow cytometric analysis of IFN-γ+ T cell responses from isolated splenocytes. Splenocytes from each animal (n=5) were isolated and individually analyzed for either NS4B-, NS5A- or NS5B-specific T cell responses. Splenocytes were stimulated with either R10 (negative control) or NS4B, NS5A or NS5B peptide pools ex vivo for 5 hours. Following incubation, cells were intracellularly stained for IFN-γ and analyzed with flow cytometry Immunization-specific responses were reported as the percent IFN-γ+ T cells in the peptide stimulated group minus the percent IFN-γ+ T cells in the R10 stimulated group. The figure shows a representative animal from each group. The values shown are the averaged response of five individual animals from both the naïve and immunized groups. Significance was determined by Student's t test (*$p<0.05$, $p<0.005$ and *$p<0.0005$).
Figure 3A:
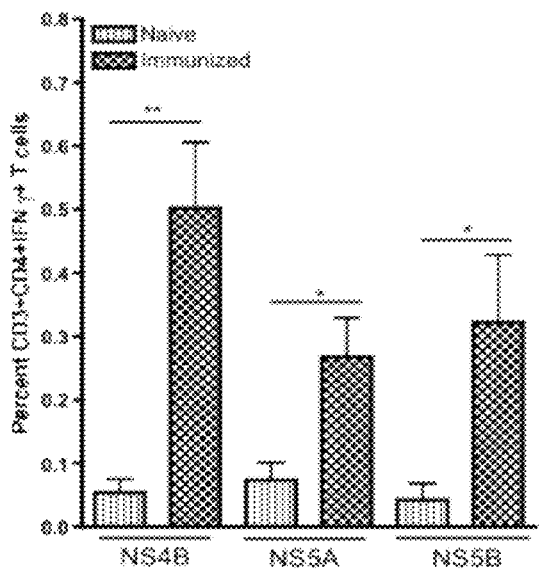
FIG. 3: Graphical representation of percent immunization-specific IFN-γ+ T cell responses from isolated splenocytes. Values are reported as A) the average percent CD4+ IFN-γ+ T cell responses and B) the average percent CD8+ IFN-γ+ T cell responses of each animal (n=5) from both the naïve and immunized groups. Significance was determined by Student's t test (*$p<0.05$, $p<0.005$ and *$p<0.0005$).
Figure 3B:
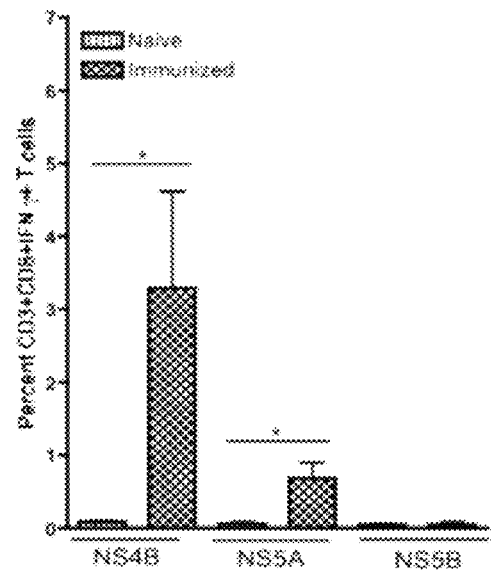

In order to determine the relative contributions of CD8+ and CD4+ T cell responses for each constructs splenocytes were intracellularly stained for IFN-γ and visualized with flow cytometry, FIG. 2. Results of the intracellular cytokine staining correlated well with those previously seen with the IFN-γ ELISpot assay. Responses for pConNS4B were the greatest, while pConNS5B was the least immunogenic. The majority of the IFN-γ responses to pConNS4B and pConNS5A was produced by CD8+ T cells, although CD4+ T cells specific for each construct were also identified. Interestingly, the majority of the IFN-γ response to pConNS5B was CD4+ T cell mediated, with few IFN-γ+CD8+ T cells identified. The average percentage of IFN-γ+CD4+ T cells for pConNS4B, pConNS5A and pConNS5B were 0.50%±0.11%, 0.27%±0.06% and 0.32%±0.11%, respectively, FIG. 3A. The average percentage of IFN-γ+CD8+ T cells for pConNS4B and pConNS5A were 3.29%±1.33% and 0.68%±0.22%, respectively, FIG. 3B.

Example 3

Immunization Induced NS4B-, NS5A- and NS5B-Specific T Cells were Detected Within the Liver Following Intramuscular Immunization Mice were immunized as previously described in Example 1, above. One week following the final immunization, the animals were sacrificed. Following sacrifice, the livers were isolated and individually pulverized using a Stomacher machine. The resulting mixture was strained and treated 5 min with 10 ml ACK lysis buffer (Bioscience) in order to clear the RBCs. The mixture was pelleted and the hepatocytes were separated from the lymphocytes through the use of a 35% percoll gradient. The pelleted lymphocytes were resuspended in complete media. Experiments were performed with and without liver perfusion, and no differences were observed.

Figure 4A:
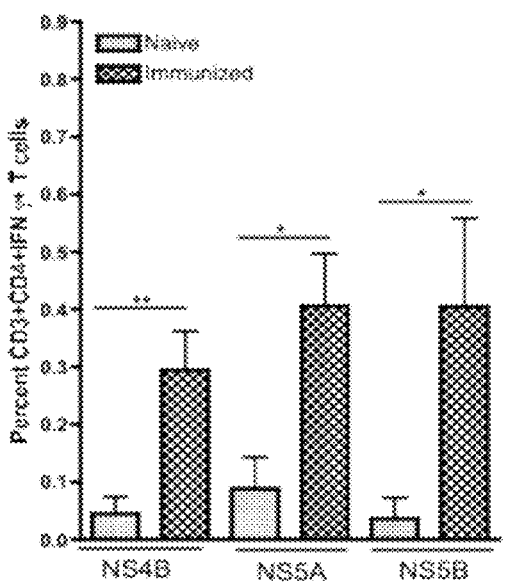
FIG. 4: Graphical representation of percent immunization-specific IFN-γ+ T cell responses from isolated liver lymphocytes. Values are reported as the average (±SE) A) percent CD4+ IFN-γ+ T cell responses and B) percent CD8+ IFN-γ+ T cell responses of each animal (n=5) from both the naïve and immunized group. Significance was determined by Student's t test (*$p<0.05$, $p<0.005$ and *$p<0.0005$).
Figure 4B:
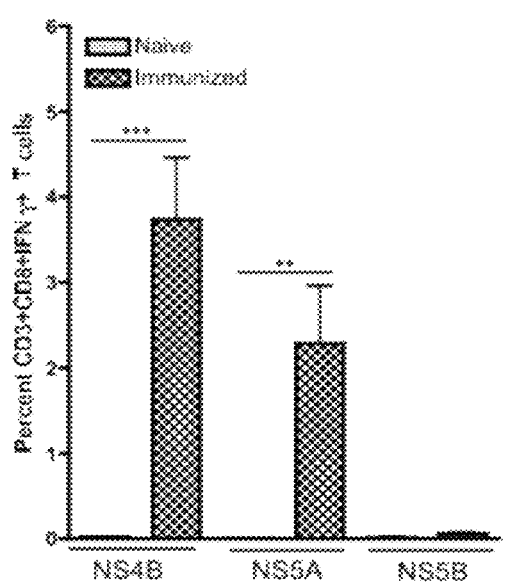

T cells were isolated from each liver and were stimulated with over-lapping peptides corresponding to each individual construct. Immunization induced HCV-specific T cells were identified by IFN-γ expression detected through intracellular cytokine staining and flow cytometry. Each animal was analyzed individually. Interestingly, HCV-specific T cells were identified in the livers of all immunized mice. Both CD4+ and CD8+ T cell responses were detected within the livers of mice immunized with pConNS4B and pConNS5A, with only CD4+ T cell responses detected in mice immunized with pConNS5B. The dominant T cell responses detected within the liver were the same as those identified within the spleen. Mice immunized with pConNS4B and pConNS5A had strong CD8+ T cell responses within the liver, while mice immunized with pConNS5B showed mainly CD4+ T cell responses and few CD8+ T cells responses. The CD4+ T cell responses for pConNS4B, pConNS5A and pConNS5B were 0.29%±0.07%, 0.41%±0.09% and 0.41%±0.06%, respectively, FIG. 4A. The CD8+ T cell responses for pConNS4B, pConNS5A and pConNS5B were 3.73%±0.73%, 2.28%±0.68% and 0.06%±0.02%, respectively, FIG. 4B.

Example 4

3.4 Liver-Specific Expression of HCV Antigens by Hepatocytes Resulted in Increased IFN-γ Production and Clearance of Transfected Hepatocytes Next we sought to determine whether liver-specific expression of either NS4B, NS5A or NS5B proteins could activate the HCV-specific T cells detected within the liver. In order to induce liver-specific expression of NS4B, NS5A and NS5B, the hepatocytes of immunized mice were transfected by administering a tail vein injection of either pConNS4B, pConNS5A or pConNS5B as previously described in Ahlen, G., et al., *In vivo clearance of hepatitis C virus nonstructural 3/4A-expressing hepatocytes by DNA vaccine primed cytotoxic T lymphocytes*. J Infect Dis, 2005. 192(12): p. 2112-6. The livers were allowed to transfect for 48 hours, after which they were harvested and the liver lymphocytes were isolated as described in Example 3, above. As mentioned before, immunization induced HCV-specific T cells were identified by IFN-γ secretion detected through intracellular cytokine staining and flow cytometry.

Intracellular Cytokine Staining

Splenocytes were resuspended in complete media at a concentration of 1×10^6 cells/100 μl and plated in a round bottom 96-well plate. Splenocytes were either stimulated with 100 μl of either: 1) 2 μg/ml pConNS4B, pConNS5A or pConNS5B overlapping peptides, 2) 1 μg/ml *Staphylococcus* enterotoxin B (positive control; Sigma-Aldrich, St. Louis, Mo.) or 3) 0.1% dimethyl sulfoxide (negative control) all diluted in complete media supplemented with GolgiStop and GolgiPlug (BD Bioscience). Splenocytes were stimulated for a total of 5 hours at 37 C following which the cells were washed three times with PBS and stained for viability. Splenocytes were stained extracellularly for surface markers; anti-CD4, CD8 for 30 min at 4 C. Following which splenocytes were permeabilized and washed using BD Cytofix/Cytoperm Solution Kit (BD Bioscience) and then stained intracellularly with anti-IFN-γ and CD3 for 45 min at 4 C. After staining, splenocytes were fixed with 1% paraformaldehyde and stored at 4 C until analysis. Specific function was reported as the percent function of the peptide stimulated group minus the percent function of the 0.1% dimethyl sulfoxide stimulated group (negative control) for each animal.

Flow Cytometry Reagents

The following directly conjugated antibodies were used: anti-mouse CD3-allophycocyanin cyanine dye 7 (APC-Cy7) [clone 145-C11], anti-mouse CD4-fluorescein isothiocyanate (FITC) [clone H129.19], anti-mouse CD8-peridinin chlorophyll protein 5.5 (PerCP5.5) [clone 53-6.7], anti-mouse IFN-γ-phycoerythryin cyanine dye 7 (PE-Cy7) [clone XMG1.2] (all from BD Biosciences, San Jose, Calif.). Aqua Live/Dead fixable dead cell Stain Kit (Molecular Probes, Eugene, Oreg.) was used according to manufactor's protocol to identify live cells.

Samples were collected on a LSR11 flow cytometer (BD Biosciences, Franklin Lakes, N.J.). BD CompBeads (BD Biosciences) and single fluorochromes were used for compensation. Data was analyzed using FlowJo software, version 8.7.1 for Mac, (Tree Star, Ashland, Oreg.).

Figure 5:
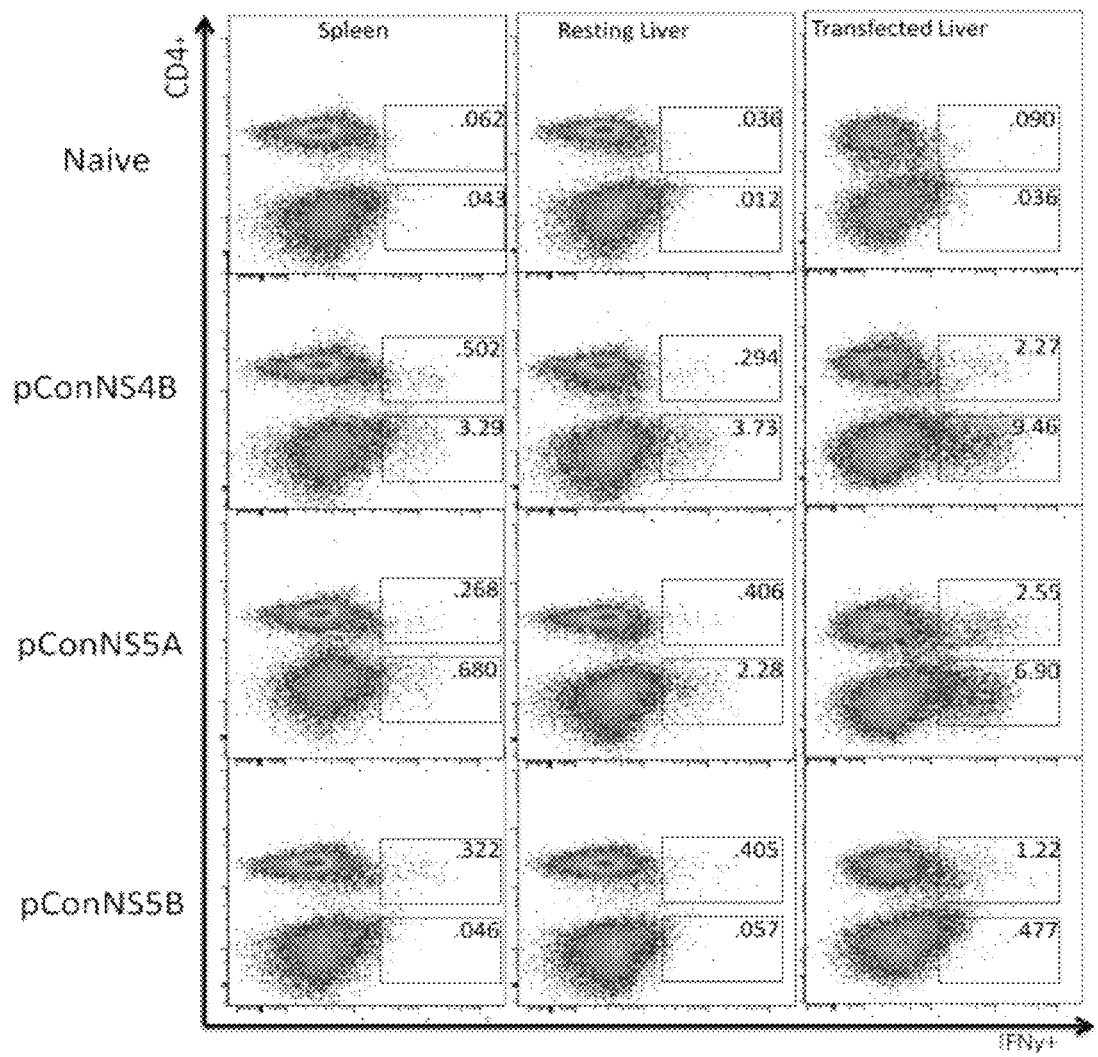
FIG. 5: Flow cytometric analysis of the percentage of IFN-γ+ T cell responses from isolated lymphocytes from the spleen, resting liver and transfected liver. Lymphocytes from each animal (n=5) were isolated and individually analyzed for either NS4B-, NS5A- or NS5B-specific T cell responses. The isolated lymphocytes were intracellularly stained for IFN-γ and analyzed with flow cytometry. The figure shows a representative animal from each group. The values shown are the averaged response (±SE) of five individual animals from both the naïve and immunized groups. Significance was determined by Student's t test (*$p<0.05$, $p<0.005$ and *$p<0.0005$).
Figures 6A, 6B, 6C, 6D, 6E, 6F:
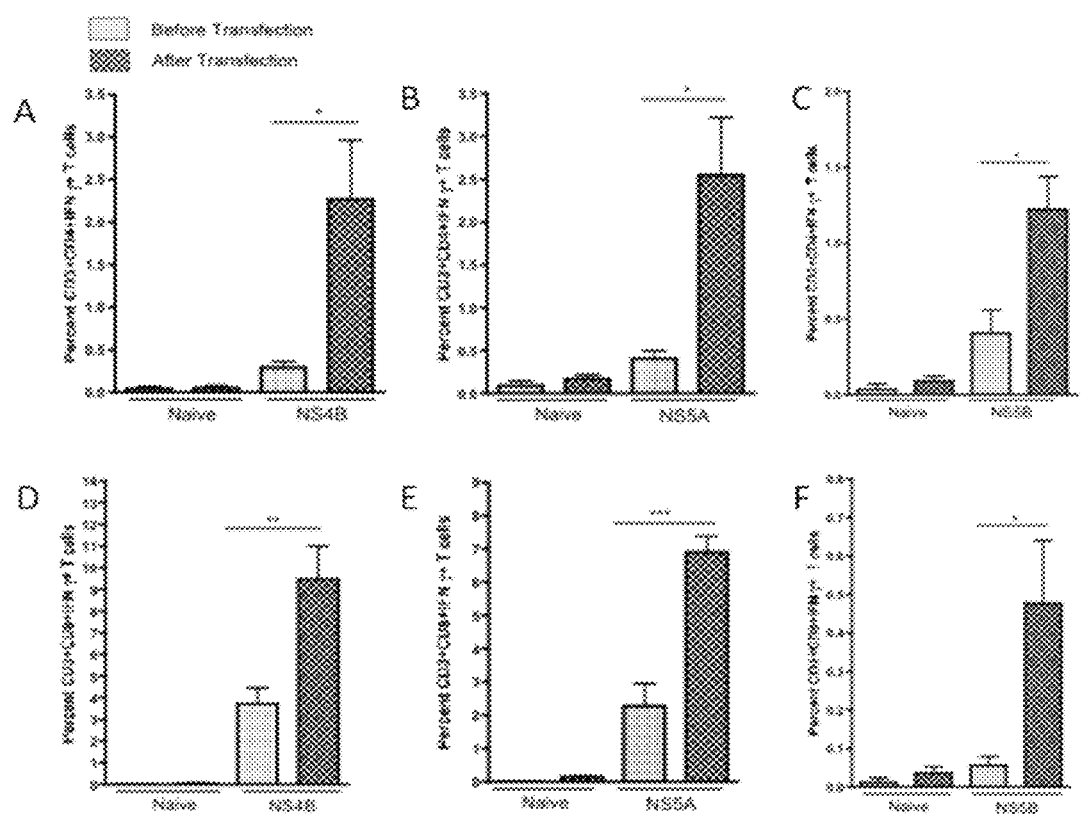
FIG. 6: Graphical representation of the percentage of IFN-γ+ T cell responses from isolated lymphocytes from the spleen, resting liver and transfected liver. Values are reported as the average percent (±SE) A) CD4+ IFN-γ+ T cell responses to pConNS4B, B) CD4+ IFN-γ+ T cell responses to pConNS5A, C) CD4+ IFN-γ+ T cell responses to pConNS5B, D) CD8+ IFN-γ+ T cell responses to pConNS4B, E) CD8+ IFN-γ+ T cell responses to pConNS5A, F) CD8+ IFN-γ+ T cell responses to pConNS5B of each animal (n=5) from both the naïve and immunized groups. Significance was determined by Student's t test (*$p<0.05$, $p<0.005$ and *$p<0.0005$).
Figures 7A, 7B, 7C:
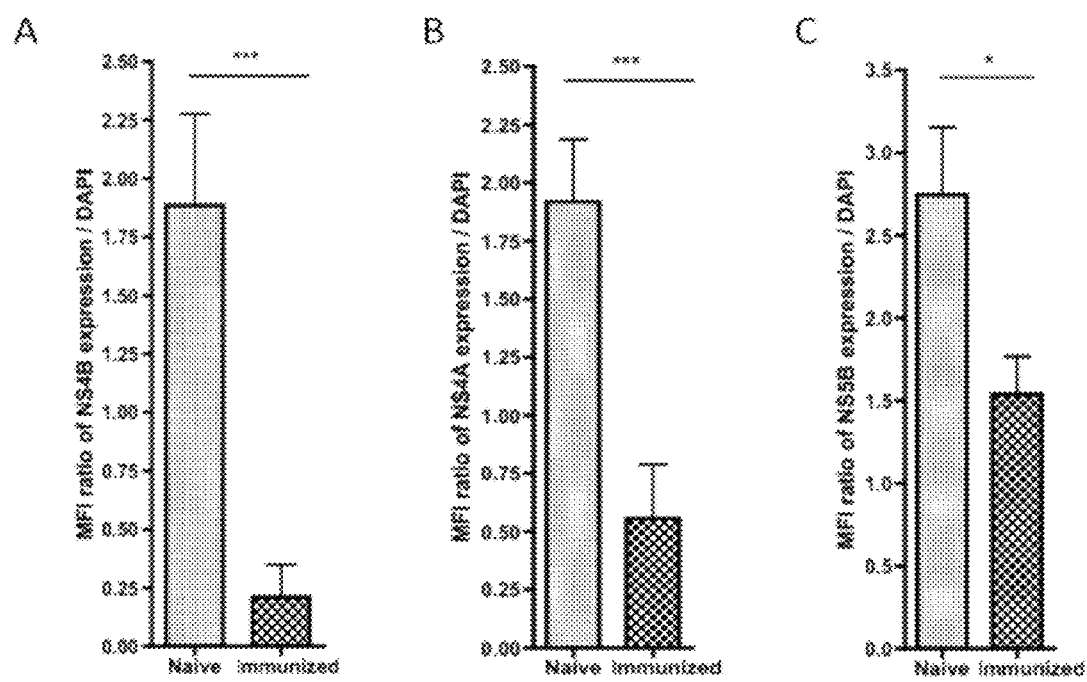
FIG. 7: Graph of MFI ratio of expression of either NS4B, NS5A or NS5B as normalized to DAPI. For each group, three images were captured for each animal (n=5). MFI values for either NS4B, NS5A or NS5B (red) were calculated and normalized to the MFI value for DAPI (blue) for each image. The values shown are the averaged response (±SE) of five individual animals from both the naïve and immunized groups. Significance was determined by Student's t test (*$p<0.05$, $p<0.005$ and *$p<0.0005$).

Following the tail vein injections, a massive increase in the percentage of both CD4+ and CD8+ HCV-specific T cells was seen in all three immunization groups as compared to the percentage of HCV-specific T cells detected in both spleen and the resting liver, FIG. 5. The percentage of CD4+ HCV-specific T cells was 2.27%±0.70%, 2.55%±0.70% and 1.22%±0.22% for mice immunized with pConNS4B, pConNS5A and pConNS5B, respectively, FIG. 6A. The percentage of CD8+ HCV-specific T cells was 9.46%±1.53%, 6.98%±0.48% and 0.477%±0.16% for mice immunized with pConNS4B, pConNS5A and pConNS5B, respectively, FIG. 6B. The largest fold increase, as determined by the percentage of HCV-specific IFN-γ+ T cells in the liver before and after tail vein injection, was seen with the CD4+ T cell response. The fold increase in the intrahepatic CD4+ T cell response in pConNS4B, pConNS5A and pConNS5B immunized mice was approximately 8, 6 and 3 fold, respectively. While the CD8+ T cell response remained the dominant response in the liver both before and after tail vein injection, a slightly smaller fold increase was seen with the CD8+ T cells response as compared to the CD4+ T cells response. The fold increase in the intrahepatic CD8+ T cell response in pConNS4B, pConNS5A and pConNS5B immunized mice was approximately 3, 3 and 8 fold, respectively.

After assessing the intrahepatic HCV-specific IFN-γ responses generated by each construct, studies were performed to determine whether immunization had generated inhepatic cytotoxic HCV-specific T cell as well. A lobe of liver was obtained from each animal in each group and was stained for hepatocyte expression of either NS4B, NS5A or NS5B. Cytotoxicity of the intrahepatic T cell response generated by immunization with each construct was assessed by the ability of each immunized animal following transfection to clear either NS4B, NS5A or NS5B expressing hepatocytes when compared to transfected immunization naïve controls. Representative confocal images of this staining for each group were observed (images not shown).

Confocal Microscopy

Livers were dissected and biopsies were fixed in 2% paraformaldehyde followed by overnight cryoprotection in 30% sucrose. Biopsies were immersed in Tissue-Tek OCT (Bayer Corporation, Pittsburgh, Pa.) and were quick frozen in 2-methyl butane on dry ice nitrogen. Staining was performed on tissue sections (6 μm) mounted on Superfrost Plus glass slides (Fisher Scientific, Pittsburgh, Pa.), and kept at 80° C. until use. Before immunofluorescent staining, slides were brought to room temperature and washed three times, 10 minutes each in phosphate-buffered saline (PBS), and blocked in PBS containing 10% normal serum of the species in which the secondary reagent was raised, and 0.1% Triton. Primary re-agents were applied to sections and incubated for 1 hour at room temperature or overnight at 4° C. The sections were washed three times, 10 minutes each in PBS, and, where necessary, secondary reagents were applied for 30 minutes at room temperature. The sections were again washed three times, 10 minutes each in PBS. Coverslips were mounted with Prolong Gold mounting media (Invitrogen, Carlsbad, Calif.) and slides kept in the dark at 4° C. until studied and photographed. All staining was performed in a humidified environment. Antibodies used were (obtained from Invitrogen or alternatively a competitor company that manufacturers antibodies. All images were obtained using a Zeiss Axiovert 100 inverted confocal microscope and analysis and quantification of florescence intensities was conducted using Image J software (NIH, Rockville, Md.).

Clearance of transfected hepatocytes for each group was quantified by the mean florescent intensity (MFI) of either NS4B, NS5A or NS5B expression normalized by the number of hepatocytes present within each field as measured by the MFI of nuclear DAPI staining, FIG. 9. Compared to the naïve control, dramatic reductions in the number of transfected heapotcytes were seen in animals immunized groups for all three constructs. Animals immunized with pConNS4B, pConNS5A or pConNS5B had approximately 9, 3 and 2 fold reductions in transfected hepatocyte expression compared to naïve controls. The amount of clearance observed in each immunization group correlated well with the HCV-specific CD8+ T cell response detected within the transfected livers. The largest amount of clearance was observed in animals immunized with pConNS4B and the least clearance was seen in pConNS5B immunized animals.

The results provided show that HCV-specific T cell induced through systemic immunization are recruited into the liver in the absence of liver-specific expression of cognate antigen leading to the formation of a large pool of intrahepatic HCV-specific T cells. These T cells remain fully functional within the liver suggesting that their recruitment to the resting liver may function instead as part of the continual process of immune surveillance and may prove to be an important mechanism by which the liver guards against infection. In support of this, in response to liver-specific expression of HCV antigens, this population of liver localized HCV-specific T cells were able to rapidly induce IFN-γ expression and clear transfected hepatocytes. Since it has been previously reported that T cell infiltration is not observed until 72 hours following liver transfection (Ahlen et al., supra), the rapid clearance of HCV transfected hepatocytes appears to be likely dependent on the liver localized HCV-specific T cell population present within the liver prior to transfection. Additionally, as seen in animals immunized with pConNS5B even a relatively small percentage of vaccine-specific responses as measured by IFN-γ production was sufficient to induce a large 2 fold reduction of transfected hepatocytes within the liver, suggesting that small percentages of vaccine-specific as detected in the periphery have the ability to exert massive effects within the liver.

Liver-induced T cell tolerance can be subverted through systemic immunization and that effective liver-specific immunity can be achieved by taking advantage of the ability of the liver to both recruit and sequester antigen-specific T cells under resting conditions. This unique property of the liver may be exploited to boost HCV-specific responses in patients already infected with the virus, as well as, to create a pool of HCV-specific T cells within the livers of naive individual that have the ability to rapidly respond and mobilize upon the first signs of infection. Taken together, the findings suggest the recruitment of antigen-specific T cells to the liver, along with preservation of their effector function within the liver may play an important and previously unappreciated role in the process of immune surveillance, which may be exploited for future T cell based HCV vaccines.

The invention claimed is:

1. A nucleic acid molecule comprising a coding sequence encoding one or more proteins selected from the group comprising:

SEQ ID NO:2; or a protein that is 98% homologous to SEQ ID NO:2.

2. The nucleic acid molecule of claim 1 encoding SEQ ID NO:2.

3. The nucleic acid molecule of claim 1, wherein the nucleic acid molecule is absent of an encoding sequence of an IgE leader having a sequence of SEQ ID NO:9.

4. The nucleic acid molecule of claim 1 comprising one or more sequences selected from the group comprising:

SEQ ID NO:1; or a coding sequence that is 98% homologous to SEQ ID NO:1.

5. The nucleic acid molecule of claim 4 comprising SEQ ID NO:1.

6. The nucleic acid molecule of claim 4, wherein the nucleic acid molecule is absent of an encoding sequence of an IgE leader, the absent encoding sequence being SEQ ID NO:7 or SEQ ID NO:8.

7. The nucleic acid molecule of claim 1 wherein the nucleic acid molecule is a plasmid.

8. The nucleic acid molecule of claim 1 wherein the nucleic acid molecule is an expression vector and sequences encoding said one more proteins are linked to regulatory elements.

9. A method of inducing an immune response in a subject, comprising administering a nucleic acid of claim 1.

10. A pharmaceutical composition comprising the nucleic acid molecule of claim 1 and a pharmaceutically acceptable excipient.

* * * * *

SEQUENCE LISTING

<160> NUMBER OF SEQ ID NOS: 9

<210> SEQ ID NO 1
<211> LENGTH: 876
<212> TYPE: DNA

<213> ORGANISM: Artificial Sequence
<220> FEATURE:
<223> OTHER INFORMATION: DNA Sequence of ConNS4B

<400> SEQUENCE: 1

```
gccaccatgg attggacctg gatcctgttc ctcgtggccg ctgccacaag agtgcacagc      60
agccagcatc tgccctacat cgaacagggc atgatgctgg ccgagcagtt caaacagaaa     120
gccctgggcc tgctgcagac agccagcaga cagggaagag gcattgcccc tgccgtgcag     180
accaactggc agaagctgga agccttctgg gccaagcaca tgtggaactt catcagcggc     240
atccagtacc tggccggcct gagcaccctg cctggcaacc ctgccattgc cagcctgatg     300
gccttcacag ccgccgtgac cagccctctg accacctccc agaccctgct gttcaacatc     360
ctgggcggat gggtggcagc ccagctggca gctcctggcg ccgctacagc ctttgtggga     420
gccggactgg ctggcgctgc catcggaagc gtgggcctgg gcaaggtgct ggtcgacatc     480
ctggccggct atggcgctgg cgtggctggg gccctggtgg cattcaagat catgagcggc     540
gaggtgccca gcaccgagga cctggtgaat ctgctgcccg ccattctgtc acctggcgct     600
ctggtggtgg agtggtctcg cccgccatc ctgagaaggc atgtcggacc tggcgaaggt     660
gccgtgcagt ggatgaaccg gctgatcgcc ttcgccagca gaggcaacca cgtgtccccc     720
acccactacg tgcctgagag cgacgccgct gccagagtga cagccatcct gtccagcctg     780
accgtgaccc agctgctgcg agactgcac cagtggatca gcagcgagtg caccaccccc     840
acctacccct acgacgtgcc cgactacgcc tgataa                               876
```

<210> SEQ ID NO 2
<211> LENGTH: 288
<212> TYPE: PRT
<213> ORGANISM: Artificial Sequence
<220> FEATURE:
<223> OTHER INFORMATION: Protein Sequence of ConNS4B

<400> SEQUENCE: 2

```
Met Asp Trp Thr Trp Ile Leu Phe Leu Val Ala Ala Ala Thr Arg Val
1               5                   10                  15

His Ser Ser Gln His Leu Pro Tyr Ile Glu Gln Gly Met Met Leu Ala
            20                  25                  30

Glu Gln Phe Lys Gln Lys Ala Leu Gly Leu Leu Gln Thr Ala Ser Arg
        35                  40                  45

Gln Gly Arg Gly Ile Ala Pro Ala Val Gln Thr Asn Trp Gln Lys Leu
    50                  55                  60

Glu Ala Phe Trp Ala Lys His Met Trp Asn Phe Ile Ser Gly Ile Gln
65                  70                  75                  80

Tyr Leu Ala Gly Leu Ser Thr Leu Pro Gly Asn Pro Ala Ile Ala Ser
                85                  90                  95

Leu Met Ala Phe Thr Ala Ala Val Thr Ser Pro Leu Thr Thr Ser Gln
            100                 105                 110

Thr Leu Leu Phe Asn Ile Leu Gly Gly Trp Val Ala Ala Gln Leu Ala
        115                 120                 125

Ala Pro Gly Ala Ala Thr Ala Phe Val Gly Ala Gly Leu Ala Gly Ala
    130                 135                 140

Ala Ile Gly Ser Val Gly Leu Gly Lys Val Leu Val Asp Ile Leu Ala
145                 150                 155                 160

Gly Tyr Gly Ala Gly Val Ala Gly Ala Leu Val Ala Phe Lys Ile Met
                165                 170                 175
```

```
Ser Gly Glu Val Pro Ser Thr Glu Asp Leu Val Asn Leu Leu Pro Ala
            180                 185                 190
Ile Leu Ser Pro Gly Ala Leu Val Val Gly Val Cys Ala Ala Ile
        195                 200                 205
Leu Arg Arg His Val Gly Pro Gly Glu Gly Ala Val Gln Trp Met Asn
    210                 215                 220
Arg Leu Ile Ala Phe Ala Ser Arg Gly Asn His Val Ser Pro Thr His
225                 230                 235                 240
Tyr Val Pro Glu Ser Asp Ala Ala Ala Arg Val Thr Ala Ile Leu Ser
                245                 250                 255
Ser Leu Thr Val Thr Gln Leu Leu Arg Arg Leu His Gln Trp Ile Ser
            260                 265                 270
Ser Glu Cys Thr Thr Pro Thr Tyr Pro Tyr Asp Val Pro Asp Tyr Ala
        275                 280                 285
```

<210> SEQ ID NO 3
<211> LENGTH: 1434
<212> TYPE: DNA
<213> ORGANISM: Artificial Sequence
<220> FEATURE:
<223> OTHER INFORMATION: DNA Sequence of ConNS5A

<400> SEQUENCE: 3

```
gccaccatgg attggacctg atcctgttc ctggtggccg ctgctaccag agtgcacagc      60
agcggctctt ggctgagaga tgtgtgggac tggatctgca ccgtgctgac cgacttcaag    120
acctggctgc agagcaagct gctgcccaga ctgcccggcg tgcccttctt cagctgccag    180
cggggctaca agggcgtgtg gagaggcgac ggcatcatgc agaccacctg tcccggcgga    240
gcccagatca ccggccacgt gaagaacggc agcatgcgga tcgtgggccc caagacctgt    300
agcaacacct ggcacggcac cttccccatc aacgcctaca ccaccggccc ttgtaccccc    360
agccctgccc ccaattacag cagagccctg tggagagtgg ccgccgagga atacgtggaa    420
gtgaccagag tgggcgactt ccactacgtg accggcatga ccaccgacaa cgtgaagtgc    480
ccctgccagg tgccagcccc cgagttcttt accgaggtgg acggcgtgag actgcacaga    540
tacgcccctg cctgcaagcc cctgctgcgg gaggaagtga ccttccaagt cggcctgaac    600
cagtacctgg tgggaagcca gctgccctgc gagcctgaac ctgacgtggc cgtgctgaca    660
agcatgctga ccgatcccag ccacatcaca gccgaggccg ctggaagaag gctcgccaga    720
ggcagccctc ctagcctggc cagcagcagc gcctctcagc tgtccgcccc tagcctgaag    780
gccacctgta ccacccacca cgacagcccc gacgccgacc tgatcgaggc caatctgctg    840
tggcggcagg aaatgggcgg caacatcacc agagtggaga gcgagaacaa ggtggtgatc    900
ctggacagct cgaccccct gagagccgaa aggacgagc gggaagtgtc cgtgcccgcc    960
gagatcctgc ggaagtcccg gaagttcccc cctgccatgc ccatctgggc cagacctgac   1020
tacaaccccc ccctgctgga aagctggaag gaccccgact acgtgcctcc tgtggtgcac   1080
ggctgccctc tgcctccaac caaggcccct cccatccccc tcccagacg aagagaacc   1140
gtggtgctga cagagtccac cgtgtctagc gccctggccg agctggccac caagaccttc   1200
ggcagcagcg agagcagcgc cgtggattct ggcacagcca ccgcccctcc cgatcagcct   1260
agcgacgacg gcgacaccgg ctccgatgtg gagagctaca gcagcatgcc ccccctggaa   1320
ggcgaacccg gcgaccctga cctgagcgac ggcagctggt ctaccgtgtc cgaggaagcc   1380
agcgaggacg tcgtgtgctg ctaccccta cgacgtgcccg actacgcctg ataa         1434
```

<210> SEQ ID NO 4
<211> LENGTH: 474
<212> TYPE: PRT
<213> ORGANISM: Artificial Sequence
<220> FEATURE:
<223> OTHER INFORMATION: Protein Sequence of ConNS5A

<400> SEQUENCE: 4

```
Met Asp Trp Thr Trp Ile Leu Phe Leu Val Ala Ala Thr Arg Val
1               5                   10                  15

His Ser Ser Gly Ser Trp Leu Arg Asp Val Trp Asp Trp Ile Cys Thr
                20                  25                  30

Val Leu Thr Asp Phe Lys Thr Trp Leu Gln Ser Lys Leu Leu Pro Arg
            35                  40                  45

Leu Pro Gly Val Pro Phe Phe Ser Cys Gln Arg Gly Tyr Lys Gly Val
        50                  55                  60

Trp Arg Gly Asp Gly Ile Met Gln Thr Thr Cys Pro Gly Gly Ala Gln
65                  70                  75                  80

Ile Thr Gly His Val Lys Asn Gly Ser Met Arg Ile Val Gly Pro Lys
                85                  90                  95

Thr Cys Ser Asn Thr Trp His Gly Thr Phe Pro Ile Asn Ala Tyr Thr
            100                 105                 110

Thr Gly Pro Cys Thr Pro Ser Pro Ala Pro Asn Tyr Ser Arg Ala Leu
        115                 120                 125

Trp Arg Val Ala Ala Glu Glu Tyr Val Glu Val Thr Arg Val Gly Asp
    130                 135                 140

Phe His Tyr Val Thr Gly Met Thr Thr Asp Asn Val Lys Cys Pro Cys
145                 150                 155                 160

Gln Val Pro Ala Pro Glu Phe Phe Thr Glu Val Asp Gly Val Arg Leu
                165                 170                 175

His Arg Tyr Ala Pro Ala Cys Lys Pro Leu Leu Arg Glu Glu Val Thr
            180                 185                 190

Phe Gln Val Gly Leu Asn Gln Tyr Leu Val Gly Ser Gln Leu Pro Cys
        195                 200                 205

Glu Pro Glu Pro Asp Val Ala Val Leu Thr Ser Met Leu Thr Asp Pro
    210                 215                 220

Ser His Ile Thr Ala Glu Ala Ala Gly Arg Arg Leu Ala Arg Gly Ser
225                 230                 235                 240

Pro Pro Ser Leu Ala Ser Ser Ala Ser Gln Leu Ser Ala Pro Ser
                245                 250                 255

Leu Lys Ala Thr Cys Thr Thr His His Asp Ser Pro Asp Ala Asp Leu
            260                 265                 270

Ile Glu Ala Asn Leu Leu Trp Arg Gln Glu Met Gly Gly Asn Ile Thr
        275                 280                 285

Arg Val Glu Ser Glu Asn Lys Val Val Ile Leu Asp Ser Phe Asp Pro
    290                 295                 300

Leu Arg Ala Glu Glu Asp Glu Arg Glu Val Ser Val Pro Ala Glu Ile
305                 310                 315                 320

Leu Arg Lys Ser Arg Lys Phe Pro Pro Ala Met Pro Ile Trp Ala Arg
                325                 330                 335

Pro Asp Tyr Asn Pro Pro Leu Leu Glu Ser Trp Lys Asp Pro Asp Tyr
            340                 345                 350

Val Pro Pro Val Val His Gly Cys Pro Leu Pro Pro Thr Lys Ala Pro
        355                 360                 365
```

```
Pro Ile Pro Pro Pro Arg Arg Lys Arg Thr Val Val Leu Thr Glu Ser
    370                 375                 380

Thr Val Ser Ser Ala Leu Ala Glu Leu Ala Thr Lys Thr Phe Gly Ser
385                 390                 395                 400

Ser Glu Ser Ser Ala Val Asp Ser Gly Thr Ala Thr Ala Pro Pro Asp
                405                 410                 415

Gln Pro Ser Asp Asp Gly Asp Thr Gly Ser Asp Val Glu Ser Tyr Ser
            420                 425                 430

Ser Met Pro Pro Leu Glu Gly Glu Pro Gly Asp Pro Asp Leu Ser Asp
        435                 440                 445

Gly Ser Trp Ser Thr Val Ser Glu Glu Ala Ser Glu Asp Val Val Cys
    450                 455                 460

Cys Tyr Pro Tyr Asp Val Pro Asp Tyr Ala
465                 470
```

<210> SEQ ID NO 5
<211> LENGTH: 1866
<212> TYPE: DNA
<213> ORGANISM: Artificial Sequence
<220> FEATURE:
<223> OTHER INFORMATION: DNA Sequence of ConNS5B

<400> SEQUENCE: 5

```
gccaccatgg attggacctg atcctgttc ctggtggccg ctgccacaag agtgcacagc    60
agcatgagct actcttggac aggcgccctg gtgacacctt gtgccgccga ggaacagaag   120
ctccccatca cgccctgag caacagcctg ctgcggcacc acaacctggt gtacagcacc   180
acctccagaa gcgcctgtca gcggcagaaa aaagtgacct tcgaccggct gcaggtgctg   240
gacagccact accaggacgt gctgaaagaa gtgaaggctg ccgccagcaa agtgaaggcc   300
aatctgctgt ccgtggagga agcctgcagc ctgacacccc tcacagcgc caagagcaag   360
ttcggctacg cgccaagga tgtgcggtgc acgccagaa aggccgtgaa ccacatcaac   420
agcgtgtgga aggatctgct ggaagatagc gtgaccccca tcgacaccac catcatggcc   480
aagaacgagg tgttctgcgt gcagcccgag aagggcggca aaagcccgc cagactgatc   540
gtgttccccg acctgggcgt gagagtgtgc gagaagatgg ccctgtacga cgtggtgtcc   600
aagctgcctc tggccgtgat gggcagcagc tacggcttcc agtacagccc tggccagcgg   660
gtggaattcc tggtgcaggc ctggaagtcc aagaaacccc ccatgggctt cagctacgac   720
accagatgct cgacagcac tgtgaccgag agcgacatcc ggaccgagga agccatctac   780
cagtgctgcg acctggaccc tcaggccaga gtggccatca gagcctgac cgagagactg   840
tacgtgggcg acctctgac aacagcaga ggcgagaact gcggcgccag aagatgtaga   900
gccagcggcg tgctgaccac ctcctgcggc aacaccctga cctgttacat caaggccaga   960
gccgcctgta gagccgccgg actgcaggac tgcaccatgc tggtgtgcgg cgacgacctg  1020
gtggtgatct gcgagtctgc cggcgtgcag gaagatgccg ccagcctgag agccttcacc  1080
gaggccatga ccagatacag cgcccctccc ggcgatcctc cccagcccga gtacgacctg  1140
gaactgatca ccagctgcag cagcaacgtg tccgtggccc acgatggcgc cggaaagcgg  1200
gtgtactacc tgaccaggga ccctaccaca cctctggcaa gggccgcttg ggagacagcc  1260
agacacaccc ccgtgaacag ctggctgggc aacatcatca tgttcgcccc cacctgtgg  1320
gcccggatga tcctgatgac ccacttcttc agcgtgctca tcgccgggga tcagctggaa  1380
caggccctgg actgcgagat ctacggcgcc tgctacagca tcgagcccct ggatctgccc  1440
```

-continued

```
cccatcatcc agagactgca cggcctgagc gccttctccc tgcacagcta cagcccaggc    1500
gagatcaaca gagtggccgc ctgcctgcgg aaactgggcg tgcctcctct gagagcctgg    1560
cggcacagag ccagatccgt gcgggccaga ctgctgtcaa gaggcggcag agcagccatc    1620
tgcggcaagt acctgttcaa ctgggccgtg cggaccaagc tgaagctgac ccctatcgcc    1680
gctgccggcc agctggatct gagcggctgg ttcacagccg gctacagcgg cggagacatc    1740
taccacagcg tgtcaagagc cagaccccgg tggttctggt tttgcctgct gctgctggcc    1800
gctggcgtgg gcatctatct gctgcccaac agataccccc acgacgtgcc cgactacgcc    1860
tgataa                                                               1866
```

<210> SEQ ID NO 6
<211> LENGTH: 618
<212> TYPE: PRT
<213> ORGANISM: Artificial Sequence
<220> FEATURE:
<223> OTHER INFORMATION: Protein Sequence of ConNS5B

<400> SEQUENCE: 6

```
Met Asp Trp Thr Trp Ile Leu Phe Leu Val Ala Ala Thr Arg Val
1               5                  10                  15

His Ser Ser Met Ser Tyr Ser Trp Thr Gly Ala Leu Val Thr Pro Cys
                20                  25                  30

Ala Ala Glu Glu Gln Lys Leu Pro Ile Asn Ala Leu Ser Asn Ser Leu
            35                  40                  45

Leu Arg His His Asn Leu Val Tyr Ser Thr Thr Ser Arg Ser Ala Cys
        50                  55                  60

Gln Arg Gln Lys Lys Val Thr Phe Asp Arg Leu Gln Val Leu Asp Ser
65                  70                  75                  80

His Tyr Gln Asp Val Leu Lys Glu Val Lys Ala Ala Ser Lys Val
                85                  90                  95

Lys Ala Asn Leu Leu Ser Val Glu Glu Ala Cys Ser Leu Thr Pro Pro
            100                 105                 110

His Ser Ala Lys Ser Lys Phe Gly Tyr Gly Ala Lys Asp Val Arg Cys
        115                 120                 125

His Ala Arg Lys Ala Val Asn His Ile Asn Ser Val Trp Lys Asp Leu
    130                 135                 140

Leu Glu Asp Ser Val Thr Pro Ile Asp Thr Thr Ile Met Ala Lys Asn
145                 150                 155                 160

Glu Val Phe Cys Val Gln Pro Glu Lys Gly Gly Arg Lys Pro Ala Arg
                165                 170                 175

Leu Ile Val Phe Pro Asp Leu Gly Val Arg Val Cys Glu Lys Met Ala
            180                 185                 190

Leu Tyr Asp Val Val Ser Lys Leu Pro Leu Ala Val Met Gly Ser Ser
        195                 200                 205

Tyr Gly Phe Gln Tyr Ser Pro Gly Gln Arg Val Glu Phe Leu Val Gln
    210                 215                 220

Ala Trp Lys Ser Lys Lys Thr Pro Met Gly Phe Ser Tyr Asp Thr Arg
225                 230                 235                 240

Cys Phe Asp Ser Thr Val Thr Glu Ser Asp Ile Arg Thr Glu Glu Ala
                245                 250                 255

Ile Tyr Gln Cys Cys Asp Leu Asp Pro Gln Ala Arg Val Ala Ile Lys
            260                 265                 270

Ser Leu Thr Glu Arg Leu Tyr Val Gly Gly Pro Leu Thr Asn Ser Arg
        275                 280                 285
```

Gly Glu Asn Cys Gly Ala Arg Arg Cys Arg Ala Ser Gly Val Leu Thr
            290                 295                 300

Thr Ser Cys Gly Asn Thr Leu Thr Cys Tyr Ile Lys Ala Arg Ala Ala
305                 310                 315                 320

Cys Arg Ala Ala Gly Leu Gln Asp Cys Thr Met Leu Val Cys Gly Asp
                325                 330                 335

Asp Leu Val Val Ile Cys Glu Ser Ala Gly Val Gln Glu Asp Ala Ala
                340                 345                 350

Ser Leu Arg Ala Phe Thr Glu Ala Met Thr Arg Tyr Ser Ala Pro Pro
            355                 360                 365

Gly Asp Pro Pro Gln Pro Glu Tyr Asp Leu Glu Leu Ile Thr Ser Cys
        370                 375                 380

Ser Ser Asn Val Ser Val Ala His Asp Gly Ala Gly Lys Arg Val Tyr
385                 390                 395                 400

Tyr Leu Thr Arg Asp Pro Thr Thr Pro Leu Ala Arg Ala Ala Trp Glu
                405                 410                 415

Thr Ala Arg His Thr Pro Val Asn Ser Trp Leu Gly Asn Ile Ile Met
                420                 425                 430

Phe Ala Pro Thr Leu Trp Ala Arg Met Ile Leu Met Thr His Phe Phe
            435                 440                 445

Ser Val Leu Ile Ala Arg Asp Gln Leu Glu Gln Ala Leu Asp Cys Glu
450                 455                 460

Ile Tyr Gly Ala Cys Tyr Ser Ile Glu Pro Leu Asp Leu Pro Pro Ile
465                 470                 475                 480

Ile Gln Arg Leu His Gly Leu Ser Ala Phe Ser Leu His Ser Tyr Ser
                485                 490                 495

Pro Gly Glu Ile Asn Arg Val Ala Ala Cys Leu Arg Lys Leu Gly Val
            500                 505                 510

Pro Pro Leu Arg Ala Trp Arg His Arg Ala Arg Ser Val Arg Ala Arg
        515                 520                 525

Leu Leu Ser Arg Gly Gly Arg Ala Ala Ile Cys Gly Lys Tyr Leu Phe
            530                 535                 540

Asn Trp Ala Val Arg Thr Lys Leu Lys Leu Thr Pro Ile Ala Ala Ala
545                 550                 555                 560

Gly Gln Leu Asp Leu Ser Gly Trp Phe Thr Ala Gly Tyr Ser Gly Gly
                565                 570                 575

Asp Ile Tyr His Ser Val Ser Arg Ala Arg Pro Arg Trp Phe Trp Phe
                580                 585                 590

Cys Leu Leu Leu Leu Ala Ala Gly Val Gly Ile Tyr Leu Leu Pro Asn
            595                 600                 605

Arg Tyr Pro Tyr Asp Val Pro Asp Tyr Ala
        610                 615

<210> SEQ ID NO 7
<211> LENGTH: 54
<212> TYPE: DNA
<213> ORGANISM: Artificial Sequence
<220> FEATURE:
<223> OTHER INFORMATION: IgE Leader DNA sequence for NS5A

<400> SEQUENCE: 7
atggattgga cctggatcct gttcctggtg gccgctgcta ccagagtgca cagc            54

<210> SEQ ID NO 8
<211> LENGTH: 54

-continued

```
<212> TYPE: DNA
<213> ORGANISM: Artificial Sequence
<220> FEATURE:
<223> OTHER INFORMATION: IgE Leader DNA sequence for NS5B and NS4B

<400> SEQUENCE: 8
atggattgga cctggatcct gttcctggtg gccgctgcca caagagtgca cagc          54

<210> SEQ ID NO 9
<211> LENGTH: 18
<212> TYPE: PRT
<213> ORGANISM: Artificial Sequence
<220> FEATURE:
<223> OTHER INFORMATION: IgE leader protein

<400> SEQUENCE: 9

Met Asp Trp Thr Trp Ile Leu Phe Leu Val Ala Ala Ala Thr Arg Val
1               5                   10                  15

His Ser
```